US011963828B2

(12) United States Patent
Haider

(10) Patent No.: US 11,963,828 B2
(45) Date of Patent: Apr. 23, 2024

(54) SURGICAL DISPLAY

(71) Applicant: Xenco Medical, LLC, San Diego, CA (US)

(72) Inventor: Jason Haider, San Diego, CA (US)

(73) Assignee: Xenco Medical, LLC, San Diego, CA (US)

(*) Notice: Subject to any disclaimer, the term of this patent is extended or adjusted under 35 U.S.C. 154(b) by 0 days.

(21) Appl. No.: 18/321,997

(22) Filed: May 23, 2023

(65) Prior Publication Data
US 2023/0310112 A1  Oct. 5, 2023

Related U.S. Application Data

(63) Continuation of application No. 17/948,861, filed on Sep. 20, 2022, now Pat. No. 11,696,813, which is a continuation of application No. 17/591,053, filed on Feb. 2, 2022, now Pat. No. 11,478,327, which is a continuation-in-part of application No. 17/331,957, filed on May 27, 2021, now Pat. No. 11,273,003.

(60) Provisional application No. 63/150,761, filed on Feb. 18, 2021.

(51) Int. Cl.
*A61B 90/00* (2016.01)
*A61B 34/00* (2016.01)

(52) U.S. Cl.
CPC .............. *A61B 90/37* (2016.02); *A61B 34/25* (2016.02); *A61B 2090/367* (2016.02); *A61B 2090/374* (2016.02); *A61B 2090/3762* (2016.02)

(58) Field of Classification Search
CPC ... A61B 90/37; A61B 34/25; A61B 2090/367; A61B 3090/374; A61B 2090/3762
See application file for complete search history.

(56) References Cited

U.S. PATENT DOCUMENTS

| 2007/0270680 | A1  | 11/2007 | Sheffer et al. |
| 2009/0080737 | A1* | 3/2009  | Battle ............... A61M 25/0662 382/131 |
| 2011/0261427 | A1  | 10/2011 | Hart et al. |
| 2013/0006095 | A1  | 1/2013  | Jenkins |
| 2014/0282008 | A1  | 9/2014  | Verard et al. |
| 2015/0264339 | A1  | 9/2015  | Reidel |
| 2018/0168741 | A1* | 6/2018  | Swayze ................. A61B 90/37 |
| 2019/0011700 | A1  | 1/2019  | Reiner |

(Continued)

FOREIGN PATENT DOCUMENTS

WO    2019/245860 A1   12/2019

OTHER PUBLICATIONS

Casari, FA, et al. (Feb. 5, 2021) "Augmented Reality in Orthopedic Surgery is Emerging from Proof of Concept Towards Clinical Studies: a Literature REview Explaining the Technology and Current State of the Art" Current Reviews in Musculoskeletal Medicine (2021) 14:192-203.

(Continued)

*Primary Examiner* — Michelle Chin
(74) *Attorney, Agent, or Firm* — Garrett H. Anderson

(57) ABSTRACT

Disclosed herein are visualization systems, methods, devices and database configurations related to the real-time depiction, in 2 D and 3 D on monitor panels as well as via 3 D holographic visualization, of the internal workings of patient surgery, such as patient intervention site posture as well as the positioning, in some cases real time positioning, of an object foreign to the patient.

17 Claims, 2 Drawing Sheets

(56) References Cited

U.S. PATENT DOCUMENTS

| | | |
|---|---|---|
| 2019/0122330 A1 | 4/2019 | Saget et al. |
| 2020/0085511 A1 | 3/2020 | Oezbek et al. |
| 2020/0334872 A1 | 10/2020 | Tripathi |
| 2020/0405396 A1 | 12/2020 | McGuan et al. |

OTHER PUBLICATIONS

Spatial Reality Display https://electronics.sony.com/spatial-reality-display/p/elfsr1 (available prior to Feb. 18, 2021).

Holographic light field display https://lookingglassfactory.com/8k (available prior to Feb. 18, 2021).

Leap Motion Controller https://www.ultraleap.com/product/leap-motion-controller/ (available prior to Feb. 18, 2021).

Medtronic StealthStation8 https://www.medtronic.com/us-en/healthcare-professionals/products/neurological/surgical-navigation-systems/stealthstation/stealthstation-s8.html (available prior to Feb. 18, 2021).

Stryker Nav3i https://www.stryker.com/us/en/navigation/products/nav3i.html (available prior to Feb. 18, 2021).

7D Surgical https://7dsurgical.com (available prior to Feb. 18, 2021).

Brainlab Spinal Navigation https://www.brainlab.com/surgery-products/overview-spinal-trauma-products/spinal-navigation/ (available prior to Feb. 18, 2021).

Nuvasive Pulse https://www.nuvasive.com/surgical-solutions/pulse/ (available prior to Feb. 18, 2021).

Globus Excelsius GPS https://www.globusmedical.com/musculoskeletal-solutions/excelsiusgps/ (available prior to Feb. 18, 2021).

Zimmer Biomet ROSA https://www.zimmerbiomet.com/medical-professionals/robotic-solutions/rosa-spine.html (available prior to Feb. 18, 2021).

NDI Polaris Vega User Guide (Feb. 2020).

Sony Spatial Reality Display (2020).

Ultraleap Hand Tracking Technical Introduction (Jun. 29, 2020).

\* cited by examiner

SURGICAL DISPLAY

CROSS-REFERENCE TO RELATED APPLICATIONS

This document claims priority to U.S. Prov. Ser. No. 63/150,761, filed Feb. 18, 2021, the disclosure of which is hereby incorporated by reference in its entirety; to U.S. application Ser. No. 17/331,957, filed May 27, 2021 which issued as U.S. Pat. No. 11,273,003 on Mar. 15, 2022, the disclosure of which is hereby incorporated by reference in its entirety, to U.S. application Ser. No. 17/591,053, filed Feb. 2, 2022, which issued as U.S. Pat. No. 11,478,327 on Oct. 25, 2022, the disclosure of which is hereby incorporated by reference in its entirety, and to U.S. application Ser. No. 17/948,861 filed Sep. 20, 2022, the disclosure of which is hereby incorporated by reference in its entirety.

BACKGROUND

Invasive surgery is a balance between a need to access an internal region and a desire to minimize disruption at that region to no more than necessary to effect the surgical goal. This balance is often skewed by the need of a surgeon to see the region that is the target of the surgery, and often to deliver a surgical insert to the region. Thus, surgery is in some cases a trade-off between gaining access, seeing one's target and actually effecting change at the site of the intervention.

A technology that reduces need to visualize the insertion site may shift this balance, so that surgeries may be completed with reduced impact on the patient, and without negatively impacting a surgeon's ability to view the site of intervention.

SUMMARY

Imaging and visualization systems are disclosed. The systems enable users to generate, view and manipulate three dimensional depictions of complex systems such as patient surgical intervention sites, and to view objects such as surgical inserts in situ at the patient intervention sites. The systems comprise one or more of a 2 dimensional display, a holographic 3 dimensional light field display, a data storage processor configured to retain configurational data for an object, such as an object representative of a surgical insert, and to receive data from which a patient surgical intervention site image may be generated, and a processor to generate such an image. Positioning the object such as a surgical insert is facilitated by position sensors such as passive position sensors that may be affixed to an object such as a surgical insert. The system further comprises an interface that obtains position information from the position sensors, and a processor capable of adjusting an image in response to position information received from the interface, for example by repositioning the object such as a surgical insert relative to the patient intervention site image. The image is adjusted, in some cases, in real time concurrently with surgery so as to present an image depicting a surgical insert in the posture which it actually is assuming ion the patient. In other cases the images are adjusted by a user pursuant to surgical planning prior to initiating surgery. Images are in some cases manipulated by a user through use of a hands-free sensor, so that a surgeon may, in real time, view and manipulate an image of a patient surgical intervention site that depicts the real time posture of a surgical insert within the patient, all without needing to touch a monitor, keyboard or touchpad, thereby keeping the surgeon's hands free for patient interaction. Images are readily observed by the 'naked eye' unaided by virtual reality optics or other headgear, further facilitating surgeon performance. Furthermore, images are presented such that multiple individuals may concurrently view an image directly. Methods related to use of these systems, and to use of images such as those that could be generated by these systems, are similarly disclosed.

Disclosed herein are imaging systems suitable for visualization of surgical procedures. Some such systems comprise one or more of: a 2 D display; a holographic light field display; a data storage processor configured to retain configurational data for an object; a plurality of passive position sensors; an interface that obtains position information from the passive position sensors; and a processor capable of adjusting an image in response to position information received from the interface. The image is 'malleable' in that it may be adjusted without replacing the configurational data, rather than being replaced by a second image drawn from a second set of configurational data captured after a surgical manipulation. Consequently image adjustment is made efficiently, rapidly, and without the need for configurational data capture equipment to be present during surgery.

In some aspects, these image systems comprise one or more of the following: a data storage processor configured to receive patient body structural data, such as wherein the patient body structural data is compatible with 2D display, wherein the patient body structural data is compatible with display on a holographic light field display, wherein the data storage processor converts 2D patient body structural data into data suitable for display on a holographic light field display, wherein the data storage processor converts data suitable for display on a holographic light field display into patient body structural data compatible with a 2D display, wherein the imaging system displays the patient body structural data, wherein the imaging system displays the patient body structural data on the 2 D display, wherein the imaging system displays the patient body structural data on the holographic light field display, wherein the imaging system concurrently displays the patient body structural data on the 2 D display and on the holographic light field display, wherein the imaging system displays the patient body structural data and the configurational data for an object, wherein the object is a surgical implant object, wherein the surgical implant object is a spinal implant object, wherein the surgical implant object is a cranial implant object, wherein the object is a surgical tool, wherein the surgical tool is a spinal surgery tool, wherein the surgical tool is a cranial surgery tool, wherein the surgical tool is a cardiac surgery tool.

In some aspects, location of the object relative to an image of the patient body structural data is informed by at least one passive position sensor of the plurality of passive position sensors. The position information in some cases exhibits one or more of the following: it is obtained from a passive position sensor on the object, is obtained from a passive position sensor on a patient, is obtained from a passive position sensor on a user, or is obtained from a passive position sensor on a hand of a user. A partial list of surgical objects includes, for example, a spinal insert, a spinal surgical tool, a cranial insert, a cranial surgical tool, a surgical insert, a surgical tool, a stent, a brace, a screw, a mechanical device, a pacemaker, an artificial bone, an artificial organ, an artificial tissue, and a transplant. In cases where the surgical object is intended for long term inclusion in a patient, the position sensor is optionally removed prior to resolution of surgery.

In some aspects, adjusting an image in response to position information received from the interface comprises rotating the image. The image adjusting in some cases exhibits one or more of the following: adjusting an image in response to position information received from the interface comprises spatially translating the image, adjusting an image in response to position information received from the interface comprises adjusting scale of the image, adjusting an image in response to position information received from the interface comprises adjusting the position of the object relative to the patient body structural data, adjusting an image does not require receipt of data from a keyboard, adjusting an image does not require receipt of data from a touchpad.

In some aspects, the system does not require imaging glasses.

In some aspects, the system does not require imaging headgear.

Also disclosed herein are methods of visualizing a patient surgery. Some such methods comprise one or more of the following elements: displaying a holographic depiction comprising a patient surgical region and a surgical object, and moving the surgical object relative to the patient surgical region in the holographic depiction.

In some aspects, the methods comprise one or more of the following elements: displaying does not require user headgear; displaying a 2 D depiction comprising the patient surgical region and the surgical object; moving the surgical object relative to the patient surgical region in the holographic depiction does not require contacting a keyboard; moving the surgical object relative to the patient surgical region in the holographic depiction does not require contacting a touchpad; moving the surgical object relative to the patient surgical region in the holographic depiction comprises receiving passive position data; moving the surgical object relative to the patient surgical region in the holographic depiction comprises physically moving a surgical object; the passive position data comprises patient surgical region passive position data; patient surgical region passive position data comprises data for a region that is not visibly accessible during surgery; the passive position data comprises surgical object passive position data; the passive position data comprises user passive position data; the surgical object comprises a spinal insert; the surgical object comprises a spinal surgical tool; the surgical object comprises a cranial insert; the surgical object comprises a cranial surgical tool; the surgical object comprises a surgical insert; the surgical object comprises a surgical tool; the method is performed prior to patient surgery; the method is performed concurrently with patient surgery; the holographic depiction comprising a patient surgical region is derived from patient MRI data; the holographic depiction comprising a patient surgical region is derived from patient X-ray data; the holographic depiction comprising a patient surgical region is derived from patient CT data.

Also disclosed herein are surgical visualization systems, such as those used to prepare for or to observe ongoing surgery. Some such systems comprise one or more of the following elements: a processor configured to receive patient image data, a file set comprising surgical object data, a 2 D patient data depiction window, a 3 D patient data depiction window, and a selection option that allows a user to introduce the surgical object data into the patient image data, thereby generating data so as to depict a 2 D image of the surgical object data introduced into the patient image data and a 3 D image of the surgical object data introduced into the patient image data.

In some aspects, the systems comprise one or more of the following elements: the patient image data comprises 2 D slices; the patient image data comprises CT data; the patient image data comprises MRI data; the patient image data comprises X-ray data; the processor converts the 2 D slices into a volumetric 3 D rendering; the surgical object data comprises at least one of a medical pedicle screw, a cervical interbody, a lumbar interbody, a cervical plate, a lumber plate and a corresponding screw; the surgical object data comprises at least one surgical device; further comprising a position sensor system; the position sensor system comprises at least one passive sensor and at least one passive sensor tracking device; at least one passive sensor is attached to a surgical instrument; a reference bracket system comprising a component attached to a patient that correlates the patient to the patient image data; the surgical instrument is displayed relative to the patient image data; concurrent 2 D depiction and 3 D depiction convey surgical instrument depth relative to the patient image data; comprising a holographic display that generates a 3 D holographic image; the holographic display depicts at least one of the patient image data, the surgical object data and the surgical instrument in the 3D holographic image; at least one of the patient image data, the surgical object data and the surgical instrument is depicted in a contrasting color; a user eye monitor that tracks user eye motion and repositions the 3D holographic image in response to user eye movement; the system does not require user headgear for a user to view the 3 D holographic image; a touch free motion controller, such as one that detects user hand position; a change in user hand position results in a change in position of the 3 D holographic image.

In some aspects the system allows hands-free manipulation of the 3 D holographic image

DETAILED DESCRIPTION

Introduction

Figure 1:
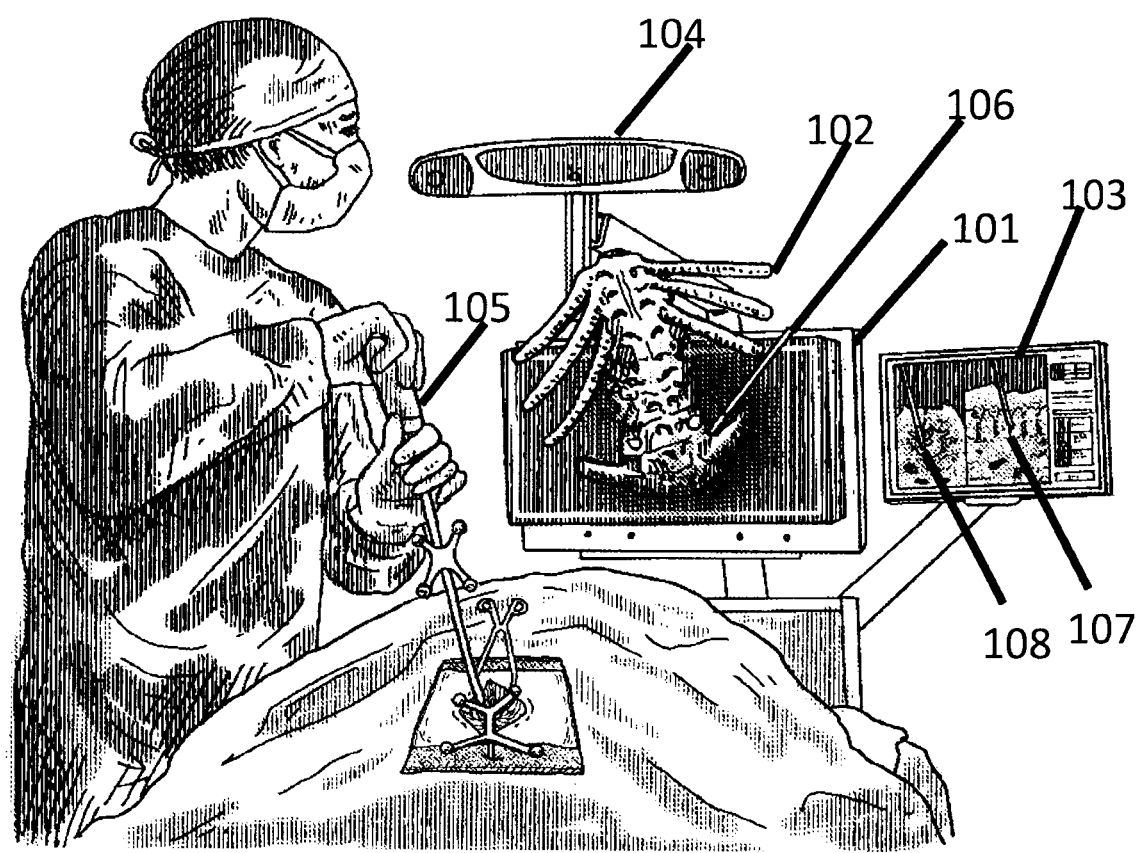
FIG. 1 depicts a surgeon using a system as described herein.

Disclosed herein are visualization systems, methods, devices and database configurations related to the real-time depiction, in 2 D and 3 D on monitor panels as well as via 3 D holographic visualization, of the internal workings of patient surgery, such as patient intervention site posture as well as the positioning, in some cases real time positioning, of an object foreign to the main image (the patient in most cases), for example a surgical insert, tool or both surgical insert and tool, relative to a patient intervention site, or of a subset of the main image relative to the remainder of the main image. Depictions are made so as to reduce a surgeon's need to directly see 'with own eyes' an intervention site, such that in some cases surgery is performed without a surgeon needing to see an intervention site directly, as well as to facilitate preparation of surgery.

The depictions generated hereby are readily manipulated, such that a surgeon may adjust the scale, orientation or other characteristics of a 2 D or 3 D monitor depiction or a 3 D holographic depiction of an intervention site or a surgical insert or surgical tool deposed therein. Manipulation is touch free in some cases, such that a user may manipulate a depiction without physically contacting a device, such as a keyboard, monitor or touchpad. Touch-free manipulation facilitates surgical economy and speed, by reducing the risk of surgeon hand contamination, and therefore the time spent ensuring hand sterilization. Touch free manipulation is accomplished through detection of user hand orientation in space, for example, or by monitoring user eye movement such that eye positioning or movement is used to direct depiction manipulation. Touch free manipulation may also be accomplished through verbal instruction by a user, such as to a voice recognition functionality. Alternate routes of manipulation, such as through foot pedals or other user motion, are also consistent with the disclosure herein. Also, in some alternate cases manipulation is effected using a conventional input such as a keyboard, mousepad or touchpad.

The technology herein is described in the context of surgical interventions, which are a preferred embodiment. Nonetheless, one will observe that the disclosure may be applied to a number of scenarios outside of surgery where a primary image is depicted as a 3 D holographic image, and a secondary image or a portion of the primary image is manipulated relative to the primary image or remainder of the primary image, such that an observer or user is able to see the spatial consequences of such a manipulation.

Data

The visualization systems, methods, devices and database configurations disclosed herein are often compatible with a broad range of data sources. Data are often provided as two dimensional slices of a patient or patient intervention site, which are computationally converted into 3 D configurations compatible with depiction of 2 D slice data as 3 D images on a monitor, or in a 3 D holographic projection, or both. Datasets, either received or converted 3 D image datasets, are often 'malleable.' in that the 2 D and 3 D images derived therefrom are adjustable, particularly in light of positional data such as that obtained through passive positional markers applied to a patient, such as a patient from which the 2 D slice data is obtained. That is, 2 D and 3 D images that are derived from a dataset, presented on screen or holographically, may be adjusted in light of positional data such as that obtained through passive positional markers applied to a patient rather than merely generating a new dataset subsequent to adjusting a patient intervention site and generating a new 2 D or 3 D image from the new data set. As dataset generation is time consuming, computationally intensive and in some cases demanding as to image collection device needed to collect the data, adjusting an image generated from the original dataset in light of passive positional markets represents a substantial improvement in speed and efficiency of image creation. Additionally, by not requiring re-imaging of a patient using an imaging device during surgery, the surgery environment is made substantially simpler, as the imaging device need not be present during surgery. This creates more room during surgery and obviates the need to ensure that am imaging device be sterilized prior to surgery. Separately, data are provided corresponding to one or more surgical insert, such as surgical inserts to be employed in a surgical procedure. Similarly, data are also provided corresponding to one or more surgical instruments, such as a surgical instrument used to deliver a surgical insert to a surgical intervention site of a patient.

Positioning of a surgical insert or a surgical instrument, or both, relative to a patient surgical intervention site is reflected in data site depictions, such as patient images, into which images of the surgical insert or a surgical instrument, or both are introduced and presented in position and orientation reflecting that of the actual surgical insert or a surgical instrument, or both, relative to the actual patient intervention site. Often, this relative positioning is informed by positional markers, such as passive positional markers. Detection of the positional markers such as the passive positional markers, is informative of the relative position of the surgical instrument or surgical insert or both relative to the patient insertion site, and of changes in the patient positioning relative to the patient positioning in the original dataset. In preferred embodiments, depiction of this positioning of one or more of patient, surgical device and surgical implant, and changes in this positioning, is effected in real time, such that the image accurately depicts the actual state of the underlying objects and patient in real time, so as to be beneficial to a surgeon performing such a procedure.

A number of 2 D slice data acquisition methods, and datasets, produced thereby, are consistent with the present disclosure. Datasets are preferably convertible into 3 D configurations for monitor and holographic display. Exemplary datasets from which 3 D images are derived include Magnetic Resonance Image (MRI) data sets and computerize tomography (CT) scan data sets, although other data sources capable of providing sectioned data slices such as ultrasound, X-ray, fluoroscopy, angiography, mammography, breast tomosynthesis, PET (positron emission tomography), SPECT (single photon emission computed tomography), endoscopy, microscopy, whole slide imaging, OCT (optical coherence tomography) are also suitable in some cases.

Data is often configured into Digital Imaging and Communications in Medicine (DICOM) format, such as DICOM 3.0, prior to delivery to a device as disclosed herein. However, the present disclosure does not in all cases require DICOM 3.0 or even alternate DICOM formatted data. Alternate formats, such as DICONDE (Digital Imaging and Communication in Nondestructive Evaluation) and other formats are compatible with some embodiments of the systems, devices and methods of the present disclosure.

Generally, data which is obtained from 2 D slices of a subject is used most often, but any data that can be configured into images of a patient is compatible with some embodiments of the present disclosure.

Similarly, data which is already configured into a format conducive to 3 D or 3 D holographic display is also compatible with the present disclosure. Surgical implants and surgical tools, such as tools for surgical implant delivery, are often configured into a format conducive to 3 D or 3 D holographic display rather than being presented as 2 D sections. Data already configured into 3 D format is also compatible with some embodiments of the present disclosure.

Computation

The visualization systems, methods, devices and database configurations disclosed herein are often reliant upon a computational system able to convert 2 D data into 3 D image datasets, and to adjust those datasets in response to additional input such as positional data regarding surgical insert or surgical instrument position data, or changes in patient posture or positioning. This additional input often arises from the detection of positional markers, such as passive positional markers, affixed to one or more of a surgical insert, a surgical instrument, or a patient.

Computational systems as disclosed herein often allow for the loading of imageable data (for example, DICOM medical image data such as CT and MRI scans, or other types as discussed herein). Data may be obtained from a remote source, wirelessly, from a drive or directly from PACS in a hospital's network. Data that is not already formatted for 3 D depiction may be subjected to one or more of segmentation, registration, and visualization.

Computational devices are often configured to translate the 2D slices of DICOM or other 2 D data formats into a volumetric 3D rendering so that the user can see both the 2D view of the data subject such as the patient's anatomy as well as a 3D view.

Computational devices are often also pre-loaded or subsequently loaded with digital files of a surgical implant or implants and optionally surgical tools such as surgical implant delivery tools, for example Medical pedicle screws, cervical and lumbar interbodies, as well as cervical and lumber plates and corresponding screws. Other surgical tools are consistent with the disclosure herein and are also contemplated. An incomplete list of surgical tools or other objects to be imaged in concert with patient data includes, for example, a stent, a brace, a screw, a mechanical device, a pacemaker, an artificial bone, an artificial organ, an artificial tissue, or a transplant tissue or organ, for example.

The user can pick specific implants and specific sizes, for example from a dropdown menu or other selection interface, and load them into the viewer with the patient anatomy. Alternately, specific implants, tools or other surgical devices may be measured so as to generate datasets suitable for their depiction in one or more of a holographic, 2 D or 3 D image as contemplated herein. Adding this material into a depiction facilitates the evaluation of various implants, tools or other surgical devices relative to each patient's anatomy, so as to help in pre-surgery implant selection or surgery strategy, for example. In some cases, in neighboring windows, the user sees both the 3D view of the implants and anatomy as well as a 2D view of the implants and anatomy simultaneously, as an alternative to or in combination with a 3 D holographic image.

Computational devices are often integrated with a position sensor apparatus such as the Polaris Vega VT Position Sensor by Northern Digital for surgical navigation, a Holographic Light Field Display for holographic visualization, and a Leap Motion controller for touch-free manipulation of the anatomy.

A beneficial feature of some computational systems disclosed herein is that adjustments to datasets, or to images depicting that data, are made in real time, such that a surgeon using the visualization systems, methods, devices and database configurations disclosed herein is able to see an up to date, volumetric image of a surgical intervention site, in multiple views on screen and in holographic projection, and to adjust the perspective or angle of view of this volumetric image, as the surgical intervention is taking place. This represents a substantial improvement over some existing technologies, where a dataset is replaced and re-collected subsequent to an adjustment to a surgical intervention site. In the present disclosure, positional information is gathered and used to adjust the image in light of a previously collected dataset. This eliminates the need for elaborate data collection instruments to be present in the surgery environment, and eliminates the need to replace entire datasets in an ongoing process throughout surgery. In its stead, data regarding the location of positional markers are gathered, and these data are used to modify the underlying patient dataset or the holographic image produced therefrom. This approach is substantially less computationally intensive, can be effected quickly with less computational burden, and requires a substantially smaller footprint in the surgery environment, which in turn facilitates a surgical environment that is more readily sterilized because large imaging machinery need not be present and re-used in multiple surgeries. More generally, the surgical environment is less cluttered, promoting a less distracting environment for a medical professional or professionals to operate.

To facilitate this real-time depiction, the image can often be manipulated in a hands-free manner, for example by a device or functionality that detects hand movements or eye movements so as to direct the depiction of the image. The real-time depiction of some embodiments, alone or in combination with the hands-free control of many embodiments, facilitates faster, more efficient surgery because the surgeon is able to see the surgical intervention site, surgical insert and perhaps surgical insertion tool from multiple angles without needing to actually directly see into the patient, and without needing to risk contamination to hands by physically touching the device to adjust the image.

Alternately or in combination, the visualization systems, methods, devices and database configurations disclosed herein may be used prior to surgery, for example as part of a surgical planning process. Such a process may comprise computational prediction of the impact or effect of a surgical insert or surgical tool on a surgical intervention site, so as to facilitate surgical insert selection and planning of the specific approach and procedure for delivery of an insert to a surgical intervention site. In some cases the image is computationally adjusted so as to simulate the effect of the surgical tools on the patient.

Alternately or in combination, the visualization systems, methods, devices and database configurations disclosed herein may be used pursuant to instruction, such as surgical instruction pursuant to surgical or medical education. Such a process may comprise real time broadcasting or broadcasting of a recorded series of surgical events or holographic images, such as to an audience. Such an audience may comprise students and in some cases an instructor, who may be present or remote to the location of the surgery. In preferred embodiments students are able to observe one or more of a planned surgical procedure or a real time depiction of a surgical procedure through observing a holographic image, alone or in combination with a 2 D or 3 D or both 2 D and 3 D depiction of a surgical intervention site.

Students are in some cases able to manipulate the holographic or other images, for example using a hands free approach as described herein or though interaction via a touchpad, keyboard, mouse, or other conventional computer interface. In particular, as preservation of a sterile environment is less critical to some instruction approaches, there may be broader flexibility as to how one interacts with an image pursuant to instruction. Alternately, in cases where simulation of a surgical environment is a priority, one may take steps or precautions in instruction that are comparable to those steps or precautions taken pursuant to actual surgery.

Adjustments to an image, either as done by a user so as to gain a desired perspective or line of site for a surgical intervention site or other site of a subject or resulting from data gathered by positional markers so as to adjust the image to reflect a surgical intervention site posture subsequent to a surgical action, for example, are in some cases recorded. Such a recording may be stored and replayed pursuant to medical instruction or to other observation of how a surgical procedure progressed.

Monitors

The visualization systems, methods, devices and database configurations disclosed herein often comprise one or more than one monitor. A monitor is used to depict data images, in either 2 D, 3 D or both 2 D and 3 D, alone or in combination with other data relevant to a surgical procedure, such as heart rate, breath rate, muscle activity, brainwave activity, or other patient data or data relevant to successful surgery. Data images are in some cases presented in real time, such that a surgeon is able to view, on a monitor, a patient surgical intervention site as it is being manipulated pursuant to surgery, for example through insertion of a surgical implant, manipulation using a surgical instrument, or both.

Alternately or in combination, data images may be used prior to surgery, for example as part of a surgical planning process. Such a process is in some cases facilitated by the 2 D and 3 D visualization on a monitor of any of a surgical intervention site, a surgical insert, and a surgical insertion tool, so as to facilitate surgical insert selection and planning of the specific approach and procedure for delivery of an insert to a surgical intervention site.

Alternately, some embodiments of the methods and systems herein do not rely upon all of 2 D and 3 D monitors and holograms. Instead, these systems rely upon some subset of these display options, such as 2 D and 3 D monitors, 2 D monitors and holograms, 3 D monitors and holograms, or 2 D monitors alone, 3 D monitors alone, or holograms alone.

Holograms

The visualization systems, methods, devices and database configurations disclosed herein often comprise one or more devices for the projection of holographic images, or the use of images so projected. Holographic images are used alone or in combination with images portrayed on monitors, as described above and elsewhere herein.

Figure 2:
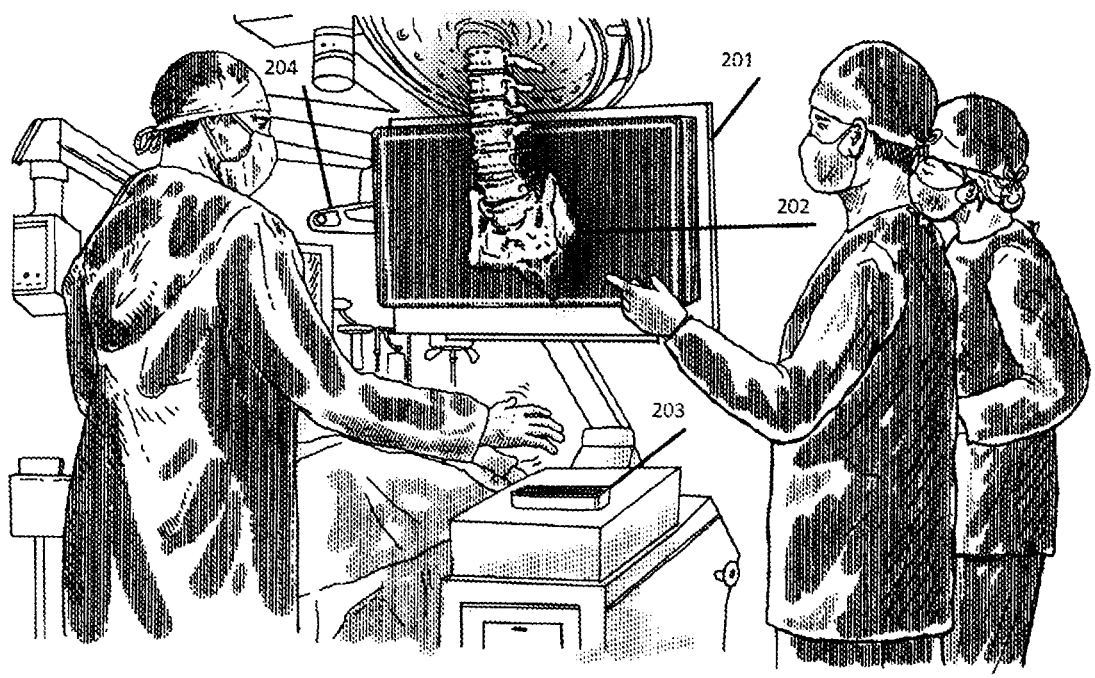
FIG. 2 depicts a surgeon using a system as described herein.

Holographic images can be projected to scale and directly in front of a user, such that they give the sense of a patient's anatomy actually hovering in air, and may be scaled, rotated or translated to change their position, or otherwise manipulated so as to facilitate viewing of a depiction of a patient anatomy. Such projections facilitate concurrent viewing by a plurality of users or medical professionals, such as depicted in FIG. 2. Holographic images may have a number of size ranges, such as at least, at most, about or exactly, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 inches, or any size in a range from or less than or exceeding 0.1×, 0.2×, 0.5×, 1×, 2×, 5× or 10× relative to an surgical target actual size.

Holographic images are often generated from data which as described above are often provided as two-dimensional slices of a patient or patient intervention site, which are computationally converted into 3 D configurations compatible with depiction of 2 D slice data as 3 D images on a monitor, or in a 3 D holographic projection, or both. Alternately, some holographic images are generated from data that is already configured for 3 D depiction or from other data types.

Holographic images consistent with the disclosure herein may comprise depictions arising from patient data alone, or both patient data and data relating to a surgical insert, a surgical tool, such as for delivery of a surgical insert, or both a surgical insert and a surgical tool, such as for delivery of a surgical instrument.

Holographic images may arise from data that is informed by positional data of a patient, or both patient data and data relating to a surgical insert, a surgical tool, such as for delivery of a surgical insert, or both a surgical insert and a surgical tool, such as for delivery of a surgical instrument. Often, positional data is obtained through the use of positional markers, such as passive positional markers, on one or more objects corresponding to or depicted in data stored on the device as disclosed herein.

The data depicted holographically is informed by positional markers such that the data images are adjusted, optionally in real time, to reflect the actual positions of the patient surgical intervention site, surgical insert or surgical tool, pursuant to surgery. By depicting the surgical environment in real time, holographically, and from an angle or perspective and scale selected by a user such as a surgeon, one is able to visualize a surgical environment without actually directly viewing the surgical intervention site in the patient. Importantly, adjustments to a holographic depiction do not require that a data set be replaced or regathered. Rather, the holographic is malleable in that it may be adjusted relative to an initial or previous image generated from underlying data, without the underlying dataset being replaced with a second data set gathered de novo pursuant to surgery. The holographic image may be adjusted in light of positional information obtained from positional markers, or alternately the data may be modified in light of positional markets and the image regenerated from the data. However, the underlying data need not be replaced in an ongoing process throughout a procedure. This malleability, either of the image relative to an initial dataset or of the dataset itself in light of positional information, allows or facilitates real time adjustment of an image, so as to facilitate its use during surgery.

Additionally, by not requiring ongoing re-gathering of patient position data pursuant to surgery, one eliminates the need for a patient data collection device (other than positional markers) to be present in a surgical environment. This results in a less crowded and more readily sterile surgical environment.

Alternately, the systems and methods herein do not in all cases preclude iterative data gathering throughout a process, as iteratively gathered data may be projected and manipulated, such as through a hands-free or conventional input approach, consistent with the remainder of the disclosure herein.

As discussed above, the perspective, scale or orientation of the holographic image may be changed, such as through a hands-free interface. Such an interface may use, for example, hand positioning or eye movement to specify changes in image depictions. Hands-fee adjustments to an image facilitates real time employment of the visualization systems, methods, devices and database configurations disclosed herein in real time in surgery.

Alternately or in combination, the visualization systems, methods, devices and database configurations disclosed herein may be used prior to surgery, for example as part of a surgical planning process, or prior to concurrent with or subsequent to surgery as part of an instructional process. Such a process is in some cases facilitated by the holographic visualization of any of a surgical intervention site, a surgical insert, and a surgical insertion tool, so as to facilitate surgical insert selection and planning of the specific approach and procedure for delivery of an insert to a surgical intervention site.

Holographic images of the present disclosure are optionally mono-color or multicolored. Multicolored holograms may display patient image and surgical insert image or surgical tool in contrasting colors. Holographic images may differentially color various parts of a patient image, such as tissues that are stretched, contorted or otherwise subjected to pressure, stress, torsion or other perturbation pursuant to or prior to surgery. Differential coloring is in some cases adjustable, such that a user may select a portion or portions of a holographic image to highlight in one or more distinct colors.

Notably, many embodiments of the holographic projection devices disclosed herein project holographic images that are readily observed by the naked eye of some users. That is, many embodiments of the holographic projections consistent with the disclosure herein do not require personal optical equipment or headgear, such that holographic images projected thereby are readily observed without the mental or ocular fatigue that is in some cases associated with holographic headgear. Particularly when used in combination with surgical interventions that last for a substantial period of time, such as hours, the reduced mental and ocular fatigue is a significant benefit to some users. Furthermore, these projections may be viewed in some cases by multiple users concurrently, as depicted in FIG. 2.

Passive Detection

The visualization systems, methods, devices and database configurations disclosed herein often present image data not only as originally received but also as modified to reflect changes in patient surgical intervention site position or posture (for example to accommodate a surgical implant or a surgical tool such as a surgical implant delivery device), as well as to reflect the introduction or change in position of a surgical implant or a surgical tool such as a surgical implant delivery device at a patient surgical intervention site.

Data indicative of such a change in position or posture of a patient or object at a site of surgical intervention is often collected through the use of a detection device or system Some such detection systems comprise delivering or affixing a detectable device to an object or solid material to be monitored such as a surgical implant or a surgical tool such as a surgical implant delivery device, or even to a patient. Some detectable devices actively send position information to an interface with a computation module of a system as disclosed herein, so as to modify an image or images in light of changes in positional information. Alternately, in some preferred embodiments, passive detectable devices are used to mark an object or solid material to be monitored such as a surgical implant or a surgical tool such as a surgical implant delivery device, or even to a patient. In these embodiments, passive detection devices such as tags work in combination with a monitoring device, such as one that actively detects passive detection tags so as to obtain additional or modifying positional information sufficient, in combination with previously obtained positional data or on its own, to modify or create new images relevant to a patient surgical intervention site. Detectable devices are variously attached to a target via an adhesive, structurally built into an or otherwise attached to an object such as a surgical insert or surgical tool such as surgical insert delivery device or adhered to a patient.

Passive detection devices are in some cases used to facilitate real-time visualization of a patient surgical intervention site, the posture of a surgical insert or surgical insert delivery tool or all of the above. By detecting changes in patient positioning or the posture of a surgical insert or surgical insert delivery tool or both, the systems and methods herein in some cases allow real time visualization on a 2 D monitor of a 2 D depiction or a 3 D depiction, or via a holographic projection, the visualization of a 3 D holograph of a surgical intervention site and surgical instrumentation in situ.

Passive detection devices as disclosed and contemplated herein allow one to make an image or patient data set to be 'malleable' such that it may be adjusted rather than throwing out or replacing a data set in its entirety subsequent to a surgical site manipulation that may change the position of a surgical instrument or patient sot or hard tissue.

Image Manipulation

The visualization systems, methods, devices and database configurations disclosed herein often present image data in a form that is readily manipulated by a user rather than being or appearing inflexible or rigid. For example, 2 D images or 3 D images on monitors or 3 D holographic images are readily manipulated in some cases, such that a user may rotate, zoom in or out, or otherwise manipulate the posture or presentation of an image. Such manipulation facilitates a user's examination of a patient surgical intervention site, alone or in combination with or adjusted to accommodate a surgical insert or a surgical tool for insertion of a surgical insert, or both.

Manipulation is effected through any of a number of approaches. Some embodiments rely upon detection of user movement, such as hand gestures. Gestures are performed at a detection site, such as over a controller, and the image is adjusted in response to the hand movement. Similarly, some devices rely upon other user movement, such as user eye movement or head movement, to direct image repositioning or reorienting Contact free input is preferred, for example, when an image is observed during surgery, such as for real-time depiction of a surgical image, so that the user's hands are free for surgical manipulations, and so that the user's hands are not at risk for desterilization through contact to an input device.

Alternately, a contact-based manipulation system such as foot pedals can be used to manipulate an object, as can more conventional approaches such as touch screens, keyboards, mouse pads or other input. Contact based input is more favorable when images are observed prior to a surgical procedure, such as in planning a surgical procedure or selecting a surgical insert or surgical tool.

Surgeries

The systems, devices and methods herein are compatible with a broad range of surgeries and medical interventions Spinal surgeries are a clear lead example, particularly due to the frequent use of surgical inserts and the inaccessibility of the surgical target region. However, a broad range of alternatives also benefit from the systems, devices and methods. Some of these procedures similarly comprise delivery of a surgical insert, in some cases to a visually removed target site. However, alternatives, some not even requiring a surgical insert, are also compatible with the present disclosure. The systems, devices and methods are compatible with, as a nonlimiting list of examples, interventions in neurology, cranial surgery, brain surgery, such as tumor removal, radiology, cardiology, oncology, nuclear medicine, radiotherapy, neurology, orthopedics, obstetrics, gynecology, ophthalmology, dentistry, maxillofacial surgery, dermatology, pathology, transplant surgery, replacement surgery, veterinary medicine, and medical/clinical photography, among others.

Methods of Patient Visualization

Devices and systems as disclosed herein are compatible with a number of methods of patient visualization. Visualization methods allow a surgeon or other medical practitioner to plan a surgical or other intervention, for example by visualizing a region or location targeted for a surgical or other intervention. Alternately or in combination, one may visualize a patient region during a surgical or other intervention, in some cases in real time Visualization approaches allow one, for example to observe the relative positioning of a surgical insert, surgical tool or even surgical target such as a tumor, herniated disc or other target, relative to other patient tissue.

Some such methods herein variously comprise depicting a patient region, including a surgical intervention target region in combination with a surgical insert or surgical tool such as a surgical insert delivery tool, and manipulating the image so as to visualize moving the surgical insert or surgical tool such as a surgical insert delivery tool relative to the patient image.

Such manipulation can be part of surgical preparation, whereby an optimal or desired surgical insert or surgical tool such as a surgical insert delivery tool position is selected ahead of a surgery.

Alternately, a surgical insert or surgical tool such as a surgical insert delivery tool can be manipulated in an image to reflect the position of the corresponding object in a patient, in some cases in real time during surgery. Real time or near real time depiction of a surgical insert or surgical tool such as a surgical insert delivery tool during surgery allows a surgeon to visualize the surgical insert or surgical tool such as a surgical insert delivery tool relative to patient tissue without directly viewing the patient tissue. A benefit to such a method is that one does not need to see a patient region, such as a recessed or not readily seen patient region, without the need to open the region to visual inspection.

Images are depicted holographically and may additionally or alternatively be presented as 2 D or 3 D images on a conventional monitor. A user, or a group of users as seen in FIG. 2, often is able to view the image without further technical supporting device such as image or method-specific headgear. Rather, the image is viewed as one would view any other image, using 'naked eye' or glasses or contacts as one would use routinely. No additional headgear, such as virtual reality or image display headgear, is needed for some embodiments of the methods disclosed herein. Alternately, practice of the methods herein does not preclude the use of headgear such as virtual reality or image display headgear, but it is not required for every embodiment.

Often, a patient surgical region and a surgical insert or surgical tool such as a surgical insert delivery tool are concurrently displayed as a hologram and as a 2 D depiction or a 3 D depiction on a more conventional monitor.

As mentioned elsewhere herein, manipulation of an image, for example rotation, translation or zooming in or out, does not in each case require contacting a device. Touch-free manipulation, whereby changes to an image are effected by hand gestures above a detection device, eye movement or other contact-free movement, is particularly useful when the method is practiced during a surgery, when a surgeon's hands are sterile and occupied in interacting with a patient. Under these conditions there is no need to contact a monitor, touchpad, keyboard or other input device.

Alternately, in some cases manipulation is effected by contacting to a physical device such as a monitor, touchpad, keyboard or other input device. Such manipulation is particularly preferred for situations where the method is practiced pursuant to surgical planning rather than execution of surgery, although use in surgery is not precluded.

Manipulation variously comprises moving the image in toto or moving a portion of the image relative to a second portion of an image, such as when one is fitting a surgical insert relative to an insertion site in a surgical planning.

Manipulation may also comprise moving a portion of an image by physically moving a component of the image and updating the image, for example in real time or near real time, to reflect the new position of the image component.

Such manipulation of the image may comprise receiving passive or active potion data from a surgical insert or surgical tool, and may comprise receiving patient passive positional data, such that the image is manipulated to reflect a change in patient tissue positioning, for example a change in patient tissue positioning that may occur in a region that is not easily directly viewed or is not visible to a surgeon.

The image manipulation may comprise movement of a portion of the image representing, for example, a spinal insert, a spinal surgical tool, a cranial insert, a cranial surgical tool, or a surgical insert, a stent, a brace, a screw, a mechanical device, a pacemaker, an artificial bone, an artificial organ, an artificial tissue, a transplant or a surgical tool or component more generally or specific to another procedure, such as a procedure as listed elsewhere herein or in regular use.

The image manipulation is performed prior to patient surgery. Alternately or in combination, manipulation is performed concurrently with surgery, such as in real time during surgery.

Images manipulated through the methods herein may be generated from MRI data, CT scan data, X-ray scan data or any data generation method mentioned elsewhere herein or known in the medical or imaging field.

Images are viewed in some cases in surgery, such that one is able to view both the image and the actual patient of which the image is a representation. That is, methods, devices and systems herein in some cases allow viewing of a holographic, or 2 D or 3 D image of a patient region, concurrently with or in alternative to viewing the physical patient surgery region. Similarly, methods, devices and systems herein in some cases allow viewing of a holographic, or 2 D or 3 D image of a surgical object as well as or in alternative to the physical surgical object, such as surgical tool or insert, for example a spinal insert, a spinal surgical tool, a cranial insert, a cranial surgical tool, a surgical insert, a surgical tool, a stent, a brace, a screw, a mechanical device, a pacemaker, an artificial bone, an artificial organ, an artificial tissue, or a transplant.

Alternately, the image is in some cases viewed by an audience remote from the surgery, such as an instructional class or even a surgeon directing a surgery remotely rather than 'in person' in the proximity of the patient. In these cases the image is viewed by an audience that may not directly look on the physical patient surgical intervention site, although they may concurrently view a 2 D or 3 D depiction of the surgical intervention site.

Aside from surgery, the methods herein fund use in other fields as well, such as any field where visualization of multiple components in a single, adjustable holographic image may be of benefit to a user. Examples include academic medical, dental or veterinary research or instruction, basic biological research such as microscopy research, engineering, architecture or other field where a manipulatable 3 D hologram, alone or in combination with a 2 D or 3 D monitor image, may facilitate comprehension or development. In such cases, the surgical implant or surgical tool is readily replaced by a tool or object compatible with the topic or research area of interest. In addition, in some cases the image to be viewed is subjected to more substantial magnification, such as a magnification of about, exactly, comparable to, or within or exceeding a rage of 2×, 5×, 10×, 20×, 50×, 100×, 200×, 500×, 1000× or more than 1000×.

Turning to the Figures, one sees the following.

At FIG. 1, one sees a surgeon using a system and practicing a method as disclosed herein. A holographic light field display 101 generates a holographic image 102. Monitor 103 presents a 2 D and a 3 D image of the subject matter of the holographic image 102. Position sensor 104 detects passive detection tags affixed to the surgical tool 105, which is introduced to the patient and is accessing the surgical intervention site. Both the holographic image 102 and the images depicted on the monitor 103 are adjusted in real time so as to depict the posture of the surgical tool 105 relative to the patient surgical intervention site. An image of the surgical tool appears, in real time, as part 106 of the holographic image 102, and as images 107 and 108 on the monitor 103.

FIG. 1 illustrates the following. Firstly, the surgical tool is presented, in real time, in the holographic image and in the monitor-presented 2 D and 3 D images of the surgical intervention site. Secondly, the surgeon does not have a direct line of sight to the surgical intervention site, but is able to view it, and the posture of the surgical tool relative to the site, via the holographic images 102 and 106, and via the monitor 103, presenting tool images 107 and 108. Thirdly, the surgeon performing the surgery does not require virtual reality or other vision supplementing headgear to view the holographic image 102 including the surgical tool image 106, or to view the monitor 103 showing surgical tool images 107 and 108, facilitating surgery performance by reducing mental or ocular fatigue.

At FIG. 2, one sees a surgeon using a system and practicing a method as disclosed herein. A holographic light field display 201 generates a holographic image 202. A gesture-based interaction sensor 203 detects hand gestures made by the surgeon, and signals a computing module to reconfigure the holographic image 202 in response to the surgeon's touch-free signals. Position sensor 204 detects passive detection tags affixed to the surgical tool, not shown. Notably, the surgeon performing the surgery does not require virtual reality or other vision supplementing headgear to view the holographic image 102 or the monitor 103, facilitating surgery performance by reducing mental or ocular fatigue. Additionally, the surgeon does not need to physically touch any device in order to manipulate the holographic image 202, facilitating ongoing surgical work by reducing risk of contaminating the surgeon's hands. The holographic image 202 is presented as if free-floating above the patient such that it may be concurrently viewed by multiple individuals.

As used herein, the term 'surgeon' refers to anyone planning, performing or directing another to perform an invasive intervention or an intervention directed to a patient. Examples of such interventions include spine surgeries comprising surgical inserts but may also include much broader instances of interventions such as administration of radiotherapy or other arguably noninvasive procedures that may nonetheless impact internal tissues or benefit from visualization or imaging of such a target region.

A surgeon is an example of a 'user,' which as used herein refers to anyone using a system or device herein or practicing a method herein. In addition to a surgeon, a user may comprise an observer of a surgery, an instructor such as a medical instructor, or any individual observing the surgical depiction as disclosed herein.

A 'holographic patient surgical region' refers to a holographic depiction of a physical patient surgical region, while a 'physical patient surgical region' refers to the actual physical site of a surgical intervention, such as patient physical tissue.

Similarly, a 'physical surgical object' refers to an actual material surgical object, such as a surgical tool or surgical implant or even a transplanted tissue or organ, while a 'holographic surgical object' refers to a holographic image of such a physical surgical object. Physical surgical objects generally are amendable to tracking using one or more positional markers, which may in some cases be removed from the surgical object subsequent to positioning in a patient if the surgery involves permanent or long term retention of the physical object in the patient.

Analogous to 'holographic patient surgical regions' and 'holographic surgical objects,' images of patient surgical regions or surgical objects may be generated for depiction on 2 D or 3 D on one or more monitors.

As used herein, the term 'about' a number refers to a range spanning +/−10% of that number. In reference to a range, the term refers to a larger range spanning from 10% below the lower listed limit of the range to 10% above the upper listed limit of the range.

As used herein, the phrase 'at least one of' A, B, and C, refers to sets comprising only A, A and B, or A, B, and C, alone or in combination with unlisted constituents.

As used herein, the term 'comprising' is pen ended, in that it does not preclude additional, unlisted elements.

EXAMPLES

Example 1. A surgeon performs spinal surgery on a patient. The patient is subjected to internal imaging, such that a dataset relating to the intervention site of the spinal surgery is available as a set of 2 Dimensional slices that collectively form a 3 Dimensional image of the intervention site.

The surgery comprises insertion of a spinal implant using a surgical tool. Dataset representations of the spinal implant and surgical tool are similarly available.

Data for the patient, implant and tool are uploaded to a visualization system. The system comprises a computational module configured to receive and manipulate all of the uploaded data, and to depict the data on a device monitor as a 2 D and 3 D image, as well as being viewable as a 3 D holographic image, optionally at 1:1 scale or a scale preferred by the surgeon.

The surgical intervention site is internal to the patient and is not easily visualized directly but is easily observed on the device monitor as a 2 D and 3 D image, as well as being viewable as a 3 D holographic image, optionally at 1:1 scale or a scale preferred by the surgeon.

The patient is labeled using passive detection tags, such that changes in patient position relative to the pre-generated dataset are measured. Using these measurements, the 2 D and 3 D monitor depictions, and the 3 D holographic image, are adjusted to reflect, in real time, the actual position of the patient and posture of the patient surgical intervention site in light of the patient position and local manipulation of the intervention site by the surgeon or others.

The surgical implant and the surgical tool are similarly labeled using passive detection tags, such that the position and orientation of the surgical implant and the surgical tool are measured. Using these measurements, the 2 D and 3 D monitor depictions, and the 3 D holographic image, are updated to reflect the position and orientation of the surgical implant and the surgical tool relative to the patient.

These updates to the datasets and to the 2 D and 3 D monitor depictions, and the 3 D holographic image, are made in real time, so that the surgeon is able to see the surgical implant and the surgical tool as they are positioned relative to the patient's intervention site.

Example 2. The surgeon performs a surgery on a patient as in Example 1 The intervention site, surgical implant and surgical tool are readily observed through the 2 D and 3 D monitor depictions, and the 3 D holographic image. As a result, the incision and impact surgical intervention site sizes are reduced through disruption of less space than is sufficient for the surgeon to directly look at all or part of the intervention site. Nonetheless, the surgeon is able to visualize the position of the spinal implant and the surgical tool by observing the surgical implant and the surgical tool, depicted in their actual positions relative to the patient intervention site, in real time.

Example 3. The surgeon performs a surgery on a patient as in Example 1 or Example 2. The depiction is available to the surgeon as a 2 D screen depiction, a 3 D screen depiction, and as a 3 D holographic image. All are presented to the surgeon such that the surgeon is able to manipulate the images without touching a keyboard, monitor or touchscreen, thereby keeping hands free and sterile for the surgery. The 3 D holographic image is viewable with the naked eye rather than through headgear, thereby reducing eyestrain and metal fatigue to the surgeon.

As a consequence, the surgery is performed with substantially reduced impact on the patient at the intervention site and with a reduced risk of contamination at the intervention site.

Example 4. The surgeon performs a surgery on a patient as in Example 1, Example 2 or Example 3. The surgery is performed remotely, such that the spinal expert surgeon is not present during the procedure. Nonetheless, the surgeon is able to direct the surgery remotely with minimal reliance on any attending health personnel who are present.

Example 5. Medical visualization software. Xenco medical visualization software allows for the loading of DICOM medical image data such as CT and MRI scans from a drive or directly from PACS in a hospital's network for segmentation, registration, and visualization. The Xenco Medical software translates the 2D slices of the DICOM into a volumetric 3D rendering so that the user can see both the 2D view of the patient's anatomy as well as a 3D view. The Xenco Medical software is also pre-loaded with digital files of Xenco Medical's spinal implants including Xenco Medical pedicle screws, cervical and lumbar interbodies, as well as cervical and lumber plates and corresponding screws. The user can pick specific Xenco Medical implants and specific sizes from a dropdown menu and load them into the viewer with the patient anatomy to evaluate various implants relative to each patient's anatomy. In neighboring windows, the user sees both the 3D view of the implants and anatomy as well as a 2D view of the implants and anatomy simultaneously. The software is integrated with the Polaris Vega VT Position Sensor by Northern Digital for surgical navigation, a Holographic Light Field Display for holographic visualization, and a Leap Motion controller for touch-free manipulation of the anatomy.

Example 6. Passive Position Sensors—Polaris Vega VT Position Sensor and passive sensors by Northern Digital. The Polaris Vega VT Position Sensor by Northern Digital allows for the real-time, intraoperative tracking of surgical instruments by tracking passive sensors which are attached to each instrument via a clip. There is a reference bracket with passive markers, which is placed on the patient. An attachment with passive sensors is placed on each instrument and they are calibrated and registered before beginning. The Polaris sensor communicates with the software by using the pre-operative CT or MRI of the patient as a reference. As the tools are moved in the field of view of the sensor, the position of the instruments, relative to the anatomy of the patient, are displayed in the software. This is especially important in gauging the depth of the surgical instrument relative to the patient's anatomy. The user is able to see the instruments relative to both the patient's 2D anatomical visualization and 3D anatomical visualization. This is also viewable on the holographic light field display, which is a separate monitor.

Example 7. Holographic Light Field display Sony Spatial Reality Display. The holographic light field display by Sony, known as their Spatial Reality Display, tracks the movement of an individual user and adjusts the 3D image in the light field based on the position of the eyes to create a hologram. The anatomical data from the Xenco Medical software, including instrument position during surgical navigation, can be viewed through the Sony Spatial Reality Display, giving the user a sense of the patient's actual anatomy hovering in air. The Sony Spatial Reality Display currently has a diagonal length of 15.6 inches. The user can manipulate the holographic anatomy through hand gestures in the air using a Leap Motion controller, a motion sensing device capable of tracking precise hand and finger movements made in the air above the controller.

Example 8. Holographic Light Field display. Looking Glass Factory 8K Display. The holographic light field display by Looking Glass Factory known as its Looking Glass 8K Display also produces holographic images but does not tracking eye movement. It also used light field display technology and currently has a diagonal length of 32 inches. The anatomical data from the Xenco Medical software, including the surgical navigation, can be viewed through the Sony Spatial Reality Display, giving the user a sense of the patient's actual anatomy hovering in air. The user can manipulate the holographic anatomy through hand gestures in the air using a Leap Motion controller, a motion sensing device capable of tracking precise hand and finger movements made in the air above the controller.

Example 9. Leap Motion Controller. The leap motion controller is a motion sensing device able to track objects with sub-millimeter accuracy. The controller allows the user to manipulate patient anatomy with hand gestures made in the air over the controller.

The following is a listing of claims related to the disclosure. It is understood that other claims are also supported by the disclosure, and that claims may change, and different claims may be recited through the course of prosecution, consistent with rights granted through this application

I claim:

1. A method of surgical procedure instruction, comprising: i) presenting, to an audience, a) a patient region image, said patient region image generated from a patient region dataset; and b) a surgical procedure instrument image, said surgical procedure instrument image generated from a surgical instrument dataset; ii) adjusting the patient region image, such that the patient region image reflects an impact of an actual surgical procedure instrument on a patient tissue of an actual patient image region; wherein the actual patient region is labeled using at least one patient region positional marker, wherein a change in position of the at least one patient region positional marker signals at least one change in the actual patient region posture, and wherein the adjusting the patient region image is generated without replacing the patient region dataset.

2. The method of claim 1, wherein the audience comprises a medical student.

3. The method of claim 1, wherein the audience comprises a medical practitioner.

4. The method of claim 1, wherein the presenting comprises projecting a holographic three dimensional depiction of the patient region image.

5. The method of claim 4, wherein the presenting comprises projecting a holographic three dimensional depiction of the surgical procedure instrument.

6. The method of claim 4, wherein the presenting comprises projecting a two dimensional depiction of the surgical procedure instrument.

7. The method of claim 1, wherein the presenting comprises projecting a two dimensional depiction of the patient region image.

8. The method of claim 1, wherein the patient image region is malleable.

9. The method of claim 8, wherein the patient image region may be manipulated through a hands-free interaction.

10. The method of claim 1, wherein the presenting is concurrent with performing the surgical procedure.

11. The method of claim 10, wherein the actual surgical instrument is labeled using at least one surgical instrument positional marker.

12. The method of claim 11, wherein the at least one surgical instrument positional marker signals at least one change in the actual surgical instrument posture.

13. The method of claim 1, wherein the presenting is subsequent to performing the surgical procedure.

14. The method of claim 1, wherein the presenting is remote to the surgical procedure.

15. The method of claim 1, wherein the presenting comprises transmission of data.

16. The method of claim 1, wherein the presenting does not comprise use of headgear.

17. The method of claim 1, wherein presenting comprises selectively changing a color or shade of the patient region image or surgical instrument image or both patient region image and surgical instrument image.

* * * * *